(12) United States Patent
Zimmermann et al.

(10) Patent No.: US 8,563,793 B2
(45) Date of Patent: Oct. 22, 2013

(54) INTEGRATED PROCESSES FOR PROPYLENE PRODUCTION AND RECOVERY

(75) Inventors: Joseph E. Zimmermann, Arlington Heights, IL (US); Larry C. Erickson, Arlington Heights, IL (US); Gregory J. Nedohin, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 542 days.

(21) Appl. No.: 12/493,374

(22) Filed: Jun. 29, 2009

(65) Prior Publication Data

US 2010/0331589 A1    Dec. 30, 2010

(51) Int. Cl.
| | | |
|---|---|---|
| C07C 5/333 | (2006.01) | |
| C07C 5/09 | (2006.01) | |
| C07C 7/04 | (2006.01) | |
| C10G 11/00 | (2006.01) | |

(52) U.S. Cl.
USPC ........... 585/302; 585/258; 585/259; 585/304; 585/654; 585/655; 585/659; 585/809; 208/113

(58) Field of Classification Search
USPC ......... 585/654, 655, 659, 304, 258, 259, 302, 585/809; 208/113
See application file for complete search history.

(56) References Cited

U.S. PATENT DOCUMENTS

| | | | | |
|---|---|---|---|---|
| 4,458,096 | A * | 7/1984 | Phillips et al. ............... | 585/302 |
| 4,675,461 | A * | 6/1987 | Owen et al. .................. | 585/330 |
| 4,695,662 | A * | 9/1987 | Vora .............................. | 585/324 |
| 4,859,308 | A | 8/1989 | Harandi et al. ............... | 208/49 |
| 4,868,342 | A * | 9/1989 | Verson .......................... | 568/697 |
| 5,302,771 | A * | 4/1994 | Venkatram et al. ........... | 585/823 |
| 5,360,533 | A * | 11/1994 | Tagamolila et al. .......... | 208/101 |
| 5,365,006 | A | 11/1994 | Serrand ......................... | 585/501 |
| 5,447,622 | A | 9/1995 | Kerby et al. .................. | 208/78 |
| 6,218,589 | B1 * | 4/2001 | Cottrell ......................... | 585/324 |
| 6,307,117 | B1 | 10/2001 | Tsunoda et al. .............. | 585/651 |
| 6,333,445 | B1 * | 12/2001 | O'Brien ......................... | 585/809 |
| 6,867,341 | B1 | 3/2005 | Abrevaya et al. ............. | 585/650 |
| 7,036,337 | B2 | 5/2006 | Wylie ............................. | 62/625 |
| 7,041,271 | B2 * | 5/2006 | Drnevich et al. .......... | 423/648.1 |
| 7,122,495 | B2 | 10/2006 | Ou et al. ........................ | 502/64 |
| 7,314,964 | B2 | 1/2008 | Abrevaya et al. ............. | 585/651 |
| 7,446,071 | B2 | 11/2008 | Abrevaya et al. ............. | 502/67 |
| 7,525,007 | B2 | 4/2009 | Sumner ......................... | 585/329 |

OTHER PUBLICATIONS

Lu et al. "Integration optimization of FCCU condensing system and gas fractionator," *Petroleum Refinery Engineering*, vol. 36 Issue 3 p. 1-5 (2006).

Mosca, et al., "Maximize propylene recovery from a FCC gas plant," *AIChE Spring National Meeting*, Conference Proceedings, May 2009.

Sloley, et al., "Polymer grade propylene from FCC C3s" *Hydrocarbon Technology International* (ISSN 0952-1399) p. 111-115 (Spring 1995).

* cited by examiner

*Primary Examiner* — In Suk Bullock
*Assistant Examiner* — Bradley Etherton
(74) *Attorney, Agent, or Firm* — Arthur E Gooding

(57) ABSTRACT

Processes utilizing the integration of (i) processes and the associated equipment used to purify and recover propylene from propane- and/or $C_4+$-containing refinery hydrocarbon streams, with (ii) catalytic dehydrogenation are disclosed. This integration allows for elimination of some or all of the conventional fractionation section of the dehydrogenation process, normally used to purify propylene from unconverted propane in the reactor effluent. Significant capital and utility savings are therefore attained.

18 Claims, 4 Drawing Sheets

INTEGRATED PROCESSES FOR PROPYLENE PRODUCTION AND RECOVERY

FIELD OF THE INVENTION

The invention relates to processes for propylene production and more particularly to the dehydrogenation of propane recovered from catalytic cracking processes such as fluid catalytic cracking (FCC).

DESCRIPTION OF RELATED ART

Propylene demand in the petrochemical industry has grown substantially, largely due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone. Currently, the majority of propylene is produced during the steam cracking or pyrolysis of hydrocarbon feedstocks such as natural gas, petroleum liquids, and carbonaceous materials (e.g., coal, recycled plastics, and organic materials), to produce ethylene. Additional significant sources of propylene are byproducts of fluid catalytic cracking (FCC) and resid fluid catalytic cracking (RFCC), normally targeting gasoline production. FCC is described, for example, in U.S. Pat. No. 4,288,688 and elsewhere. A mixed, olefinic $C_3/C_4$ byproduct stream of FCC may be purified in propylene to polymer grade specifications by the separation of $C_4$ hydrocarbons, propane, ethane, and other compounds.

Much of the current propylene production is therefore not "on purpose," but as a byproduct of ethylene and gasoline production. This leads to difficulties in coupling propylene production capacity with its demand in the marketplace. Moreover, much of the new steam cracking capacity will be based on using ethane as a feedstock, which typically produces only ethylene as a final product. Some hydrocarbons heavier than ethylene are present, but generally not in quantities sufficient to allow for their recovery in an economical manner. In view of the current high growth rate of propylene demand, this reduced quantity of co-produced propylene from steam cracking will only serve to accelerate the value of propylene in the marketplace.

More recently, the desire for propylene and other light olefins from alternative, non-petroleum based feeds has led to the use of oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. The yield of light olefins from such a process may be improved using olefin cracking to convert some or all of the $C_4+$ product of MTO in an olefin cracking reactor, as described in U.S. Pat. No. 7,268,265. Other processes for the targeted production of light olefins involve high severity catalytic cracking of naphtha and other hydrocarbon fractions. A catalytic naphtha cracking process of commercial importance is described in U.S. Pat. No. 6,867,341.

Paraffin dehydrogenation represents yet another dedicated route to light olefins and is described in U.S. Pat. No. 3,978,150 and elsewhere. However, the significant capital cost of a propane dehydrogenation plant is normally justified only in cases of large-scale propylene production units (e.g., typically 250,000 metric tons per year or more). The substantial supply of propane feedstock required to main this capacity is typically available from propane-rich liquefied petroleum gas (LPG) streams from gas plant sources.

Despite the variety of both dedicated and non-dedicated routes for generating light olefins industrially, the demand for propylene in particular is outpacing the capacity of such conventional processes. Moreover, further demand growth for propylene is expected. A need therefore exists for cost-effective methods that can increase propylene yields from existing refinery feed sources that are not necessarily of the scale of commercial LPG streams from natural gas production.

SUMMARY OF THE INVENTION

The invention is associated with the discovery of economical processes for propylene production, and particularly those in which impure propane in refinery streams is separated from a purified propylene fraction, as the main product, and optionally other components.

The separated propane is dehydrogenated, often to extinction or near extinction in a recycle loop (i.e., to effect complete or nearly complete propane conversion). A particular refinery stream of interest, which often forms at least part of the hydrocarbon feed to the processes described herein, is a propylene- and propane-containing product of a catalytic cracking process such as fluid catalytic cracking (FCC) or resid catalytic cracking (RFCC). For example, a byproduct fraction containing $C_3$ and $C_4$ hydrocarbons is normally obtained from an FCC gas concentration section that is fed by overhead vapors from the FCC main fractionation column. This byproduct is rich in $C_3$ and $C_4$ olefins due to the upstream cracking reactions being carried out in the absence of added hydrogen.

Aspects of the invention relate to the integration of (i) processes and the associated equipment used to purify and recover propylene from propane- and/or $C_4+$-containing refinery hydrocarbon streams, with (ii) catalytic dehydrogenation. This integration allows for elimination of the conventional fractionation section of the dehydrogenation process, normally used to purify propylene from unconverted propane and other components in the reactor effluent. Significant capital and utility savings are therefore attained, due to the substantial energy and equipment requirements associated with this separation. The "sharing" of major separation equipment, which may include a depropanizer, a deethanizer, and/or a propane/propylene splitter, between propylene recovery and catalytic dehydrogenation processes provides important cost benefits relative to carrying out these processes separately.

In particular, combining process streams that benefit, in the integrated processes described herein, from being treated in a similar manner allows for the realization of economies of scale. That is, the added costs for larger capacity equipment (e.g., distillation columns) and its operation in processing combined propylene-containing streams is significantly less than that of duplicating at least some of the same or similar equipment in separate processes. Moreover, the use of integrated processes can, in some cases, render smaller capacity catalytic dehydrogenation units economically feasible when coupled with existing or planned propylene recovery processes.

According to particular embodiments, therefore, integrated methods for propylene production comprise processing, in a propylene recovery unit (PRU), a hydrocarbon feed comprising propylene-containing products of both catalytic cracking and catalytic dehydrogenation processes. Products of the propylene recovery, or PRU products, include a purified propylene fraction and a purified propane fraction. Advantageously, the purified propane is passed to the catalytic dehydrogenation process to convert at least a portion of the separated propane to higher-value propylene. This converted propylene is therefore contained in the catalytic dehydrogenation reactor effluent, which is namely the propylene-containing product that is recycled back to the PRU. Therefore, while the per-pass conversion of propane, in the catalytic dehydrogenation reaction zone(s) is equilibrium limited, the integrated processes described herein may achieve complete or nearly complete overall conversion of propane originating from the propylene-containing product of catalytic cracking and/or other propylene- and propane-containing products. In particular embodiments, at least a portion of the propane that is converted is obtained from a fluid catalytic cracking (FCC) process.

A representative PRU comprises a fractionation section for the removal of lighter (e.g., $C_2-$) and heavier (e.g., $C_4+$) hydrocarbons, as well as propane, from the hydrocarbon feed, in order to provide the purified propylene fraction. The fractionation section typically comprises one or more fractionation or distillation columns including a depropanizer (e.g., a $C_3/C_4$ splitter), a deethanizer, and/or a propane/propylene splitter. In one embodiment, therefore, a depropanizer, a deethanizer, and a propane/propylene splitter are used in series, such that the hydrocarbon feed is passed to a depropanizer; a low-boiling depropanizer fraction (e.g., a depropanizer overhead) enriched in propylene, propane, and $C_2-$ hydrocarbons is passed to the deethanizer; and a high-boiling deethanizer fraction (e.g., a deethanizer bottoms) enriched in propylene and propane is passed to the propane/propylene splitter to provide the purified propylene fraction as a low-boiling propane/propylene splitter fraction (e.g., a propane/propylene splitter overhead).

In another embodiment, a suitable PRU may comprise the distillation columns noted above, but in the order of deethanizer, propylene/propane splitter, and depropanizer, in a manner similar to that in some catalytic dehydrogenation processes (but without an added propylene-containing product of a catalytic cracking process (e.g., FCC)) for the downstream fractionation of the reactor effluent. In either case, products of the PRU, in addition to the purified propylene and purified propane fractions, are fractions enriched in $C_4+$ hydrocarbons (e.g., $C_4$ olefins) and $C_2-$ hydrocarbons (e.g., ethylene) that may be removed from the integrated process. The PRU, in addition to the fractionation section, generally also comprises a treating section for removing various contaminants from the purified propylene fraction in order to meet polymer-grade specifications. A number of other configurations of the PRU are possible.

These and other aspects and embodiments associated with the present invention are apparent from the following Detailed Description.

BRIEF DESCRIPTION OF THE DRAWINGS

FIGS. 1-4 are to be understood to present an illustration of the invention and/or principles involved. Details including pumps, compressors, various heaters and heat exchangers, reboilers, condensers, instrumentation and control loops, and other items not essential to the understanding of the invention are not shown. As is readily apparent to one of skill in the art having knowledge of the present disclosure, propylene production methods involving the integration of a catalytic dehydrogenation process with a PRU and optionally a catalytic cracking process according to various other embodiments of the invention have configurations, equipment, and operating parameters determined, in part, by the specific hydrocarbon feedstocks, products, and product quality specifications.

DETAILED DESCRIPTION

Figure 1:
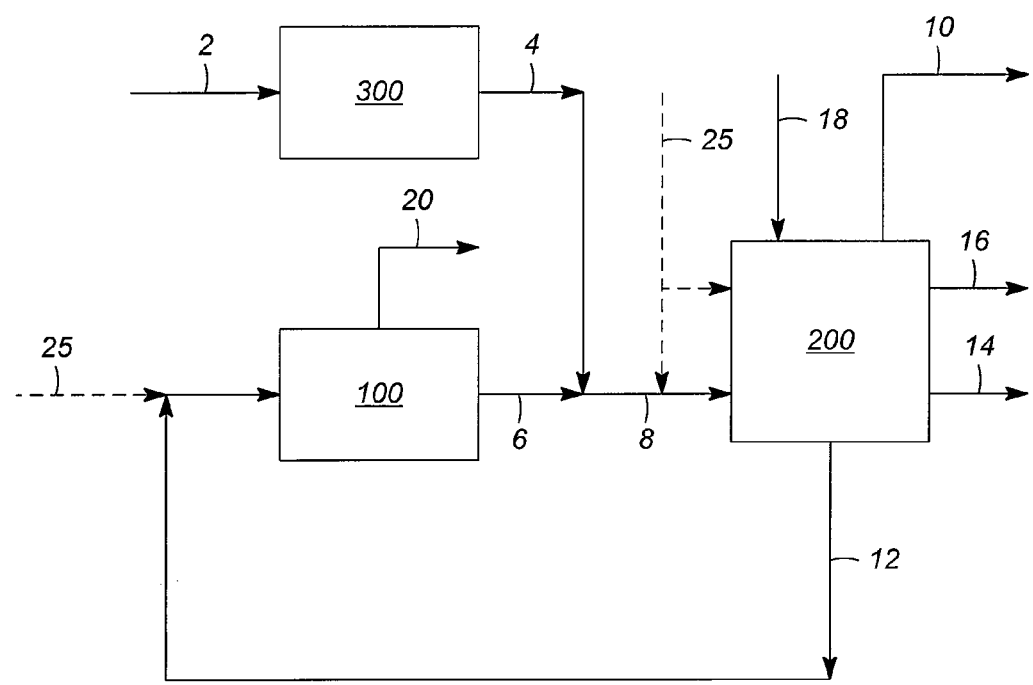
FIG. 1 depicts a representative overall process in which a propylene recovery unit (PRU) is integrated with a catalytic dehydrogenation process is integrated.

As discussed above, the present invention is associated with integrated processes for propylene production and recovery in which propylene-containing refinery and/or petrochemical streams are processed in a propylene recovery unit (PRU) that is integrated with a catalytic dehydrogenation process, such that substantial capital and/or operating cost savings may be realized. Representative propylene-containing products include those from catalytic cracking (e.g., FCC), as well as the catalytic dehydrogenation process. These products may be combined and passed to a distillation column (e.g., a depropanizer) of the PRU as a single hydrocarbon feed. Alternatively, the propylene-containing products, as components of the hydrocarbon feed, may be passed to separate sections of a distillation column, for example, fed to different column trays corresponding to different vertical or axial inlet positions, according to their compositions. Overall, therefore, integrated processes according to the present invention comprise introducing a propylene-containing product, other than one obtained from a catalytic dehydrogenation process, into the integrated process recycle loop in which (1) a PRU is used to recover and possibly treat a purified propylene fraction and thereby separate a purified propane fraction and (2) a catalytic dehydrogenation reaction zone is used to produce propylene from the purified propane fraction and thereby provide a catalytic dehydrogenation reaction zone effluent, a fraction of which is recovered from the catalytic dehydrogenation process and passed back to the PRU.

The propylene-containing product of the catalytic dehydrogenation process, as a component of the hydrocarbon feed, may therefore be a fraction comprising propylene and propane, of the total dehydrogenation reaction zone effluent. The fraction may be obtained as a liquid, for example from the separation of the dehydrogenation reaction zone effluent at high pressure and/or using a cryogenic separation system. With cryogenic separation, the liquid fraction is generally recovered at a representative temperature from about $-200°$ F. ($-129°$ C.) to about $-20°$ F. ($-29°$ C.) and at a pressure from about 7 kPa (1 psig) to about 340 kPa (50 psig). This liquid fraction typically contains substantially all $C_3$ and heavier hydrocarbons exiting the catalyst dehydrogenation reaction zone, with a representative liquid fraction containing from about 20% to about 35% by weight propylene due to the equilibrium limitations of the per-pass conversion, as well as the formation of non-selective reaction products (e.g., cracked, light hydrocarbons such as ethane, in addition to diolefins, and $C_4+$ hydrocarbons). The balance of this liquid fraction, obtained after the separation and removal of a hydrogen-rich vapor fraction as discussed below, is therefore predominantly unconverted propane, present in an amount normally from about 50% to about 85% by weight.

A vapor fraction comprising predominantly hydrogen (e.g., in an amount from about 85% to about 93% by volume) is also normally separated and then divided into recycled and non-recycled portions, with the latter being a net separator off gas containing the net hydrogen produced in the catalytic dehydrogenation process. The recycled portion of the vapor fraction is usually combined with the propane feed to the catalytic dehydrogenation process, namely the purified propane fraction obtained from the PRU.

Other propylene-containing products of catalytic dehydrogenation may be obtained after further processing of the fraction of the total dehydrogenation reaction zone effluent, containing predominantly propane and propylene, in the PRU. For example, representative products of catalytic dehydrogenation are those in the recycle loop of the overall integrated process as described above. Therefore, the low-boiling depropanizer fraction or the high boiling deethanizer fraction, as discussed above, are also suitable propylene-containing products of catalytic dehydrogenation, with which a propylene-containing product of a catalytic cracking process may be combined (e.g., either prior to or within a fractionation column of the PRU) as components of the hydrocarbon feed that is processed in the PRU as described herein. That is, the propylene-containing product of catalytic cracking can be added at various points in the recycle loop of the integrated process. In the cases of a PRU comprising either (i) a depropanizer, a deethanizer, and a propane/propylene splitter used in series (from the upstream end to the downstream end) or (ii) a deethanizer, a propylene/propane splitter, and a depropanizer in series, the propylene-containing product of catalytic cracking is preferably combined with the propylene-containing product of catalytic dehydrogenation that is obtained as a liquid fraction of the dehydrogenation reaction zone effluent, as discussed above.

Examples of catalytic dehydrogenation processes for the manufacture of light olefins such as propylene are described, for example, in U.S. Pat. No. 3,978,150 and elsewhere. In representative processes for the dehydrogenation of propane, a propane-containing feed gas stream is preheated to a temperature usually in the range from about 600° C. (1112° F.) to about 700° C. (1292° F.). Dehydrogenation occurs in a reaction zone comprising at least one, but often several, dehydrogenation reactors containing moving beds of catalyst (e.g., comprising platinum on alumina), to obtain a dehydrogenation effluent that is normally a gas stream comprising predominantly propane, propylene, hydrogen, and the non-selective reaction products (or byproducts) as discussed above. The dehydrogenation reactors are normally maintained at an absolute pressure from about 50 kPa (7 psia) to about 2 MPa (290 psia), preferably from about 100 kPa (15 psia) to about 1 MPa (145 psia). The dehydrogenation reaction zone effluent, exiting the last dehydrogenation reactor, is generally cooled and compressed in a plurality of stages of a cryogenic separation system. The liquid fraction of the dehydrogenation reaction zone effluent discussed above is substantially separated from hydrogen and byproduct methane, by condensation in a "cold box."

The use of multiple reactors and interstage heating between these reactors in the dehydrogenation reaction zone is a preferred mode of operating the catalytic dehydrogenation process, due to the primary dehydrogenation reaction being endothermic. Also, the use of moving reactor beds allows for continuous catalyst regeneration (CCR) in which spent catalyst is continuously withdrawn from the final reactor, regenerated by combustion of deposited coke in a separate oxygen-containing, regenerator atmosphere, and recycled as regenerated catalyst back to the first reactor of the dehydrogenation reaction zone.

According to embodiments of the invention a separate, propylene-containing product of catalytic cracking is processed in the PRU together with the propylene-containing product of catalytic dehydrogenation as discussed above. Commonly used processes for catalytic cracking that generate propylene-containing products such as LPG comprising propylene and $C_4$ olefins include fluid catalytic cracking (FCC) and resid catalytic cracking (RCC) processes. FCC is well known and described, for example, in U.S. Pat. Nos. 4,923,594, 4,632,749, 4,337,145, 4,247,845, 4,234,411, 4,051,013, and other references. Depending on the particular separation used, the total quantity of propylene and $C_4$ olefins in the LPG from FCC is normally at least about 50%, and often at least about 75% (e.g., in the range from about 75% to about 99%) by weight.

Heavy hydrocarbon feedstocks that may be subjected to catalytic cracking such as FCC may comprise high boiling fractions of crude oil. These include atmospheric and vacuum gas oil (VGO) (e.g., light vacuum gas oil (LVGO) and heavy vacuum gas oil (HVGO)) recovered from crude oil fractionation. Other heavy hydrocarbon feedstocks, or components thereof, include residual oils such as crude oil atmospheric distillation column residues (e.g., boiling above about 343° C. (650° F.)), crude oil vacuum distillation column residues (e.g., boiling above 566° C. (1050° F.)), tars, bitumen, coal oils, shale oils, and Fischer-Tropsch wax. Whole or topped petroleum crude oils such as heavy crude oils may also be used as all or a part of a heavy hydrocarbon feedstock, as well as other straight run and processed hydrocarbon streams that can benefit from a reduction in molecular weight to produce more valuable cracked products (e.g., gasoline boiling range hydrocarbons and LPG comprising propylene and $C_4$ olefins). Other refractory hydrocarbon streams containing predominantly hydrocarbons boiling in the range from about 343° C. (650° F.) to about 593° C. (1100° F.) may be used. Heavy hydrocarbon feedstocks may comprise combinations of any two or more of the above streams. Heavy hydrocarbon feedstocks will therefore generally contain a substantial amount, for example at least about 60%, typically at least about 90%, and often at least about 95% by volume, of hydrocarbons boiling at greater than a representative cutoff temperature for a crude oil atmospheric column residue, for example 343° C. (650° F.).

In a representative FCC process, the heavy hydrocarbon feedstock, with VGO being representative, contacts a cracking catalyst having a fine particle size in an FCC reaction zone in a fluidized manner. The cracking catalyst generally comprises one of a class of aluminosilicate molecular sieves known as zeolites, which are described in detail by D. W. Breck, *Zeolite Molecular Sieves*, John Wiley and Sons, New York (1974), and elsewhere. The fluidized reaction mixture of FCC catalyst and hydrocarbon feedstock normally flows upwardly through the reaction zone, possibly together with a diluent gas added to obtain the proper flow conditions for fluidization. Suitable diluent gases include non-oxidative gases that are relatively inert in the FCC process, such as nitrogen, argon, carbon dioxide, steam, methane, and mixtures of these gases. Adding a diluent such as steam or other inert gas lowers the partial pressure of the reactant hydrocarbons, while generally maintaining the operating temperature and pressure of the system.

At the inlet of the FCC reaction zone, a typical weight ratio of catalyst to heavy hydrocarbon feed (or "catalyst to oil ratio") is from about 2 to about 50, and is often from about 3 to about 25. Normally, the reaction zone is in the form of a riser reactor, in which catalyst and hydrocarbons are contacted in the proper ratio and under proper conditions of temperature, pressure, and residence time to achieve a desired conversion level for a given feed. Representative conditions in the reaction zone to convert high boiling hydrocarbons in the heavy hydrocarbon feedstock to lower boiling hydrocarbons (e.g., in the gasoline boiling range or lighter) include a temperature from about 450° C. (842° F.) to about 700° C. (1292° F.), often from about 500° C. (932° F.) to about 565° C. (1050° F.), and a pressure from about 7 kPa barg (1 psig) to about 345 kPa (50 psig), often from about 70 kPa (10 psig) to about 210 kpa (30 psig).

Representative FCC processes are operated with a dynamic heat balance, whereby heat is supplied to the reaction zone by a hot, regenerated catalyst exiting a regeneration zone. An integral part of the FCC process therefore involves separating and removing spent or coked catalyst composition from the reaction zone after reaction to combust deposited coke in the regeneration zone. Both (i) the coke formed in the fluidized reaction mixture as a byproduct of the desired catalytic cracking reactions, and (ii) metal contaminants in the heavy hydrocarbon feed stream, serve to deactivate the FCC catalyst by blocking its active sites. Coke must therefore be removed to a desired degree by regeneration, which involves contacting the catalyst composition in its spent or coked form with a regeneration gas stream containing oxygen, typically air or nitrogen-enriched air having a reduced oxygen content. The combustion of accumulated coke on the spent catalyst composition provides a regenerated catalyst composition, typically having a level of deposited coke of less than about 3%, and often less than about 1% by weight.

The severity of conditions in the reaction zone can be varied to obtain a desirable slate of products, which normally include $C_1$-$C_4$ hydrocarbons and gasoline boiling range hydrocarbons. Gasoline boiling range hydrocarbons can include, for example, $C_5$+ hydrocarbons having a distillation temperature of 380° F. (193° C.) at the 90% end point, according to ASTM D-86. Reaction zone severity can be increased or decreased to provide, respectively, mostly distillate boiling range hydrocarbons, or mostly $C_4^-$ hydrocarbons, and particularly valuable olefinic hydrocarbons such as propylene. Regardless of the operating severity, the product hydrocarbons in the effluent stream, having a reduced boiling point, are separated in a product recovery section, normally including an FCC main column, optionally in combination with additional distillation columns and/or flash separators providing one or multiple stages of vapor-liquid contacting (e.g., distillation stages) to separate products on the basis of differences in relative volatility.

For example, the main column can separate gasoline boiling range hydrocarbons from the reactor effluent as an FCC gasoline product stream along with other products. The FCC gasoline product may be debutanized, such that it contains, for example, less than about 3%, and often less than about 1%, by volume of $C_4$ and lighter hydrocarbons. A $C_4^-$ hydrocarbon stream can therefore be separately recovered from the reactor effluent, with this stream typically being further fractionated into fuel gas and more valuable $C_3$/$C_4$ hydrocarbons as an LPG comprising a significant amount of propylene and $C_4$ olefins as discussed above. This propylene-containing product of FCC is therefore a desirable component of the hydrocarbon feed that is processed in the PRU according to embodiments of the invention.

Other products of catalytic cracking, and FCC in particular, include fractions containing higher boiling hydrocarbons, compared to those in an FCC gasoline product stream. Examples of such products are heavy naphtha and light cycle oil. According to some embodiments, unconverted hydrocarbons exiting the main column, for example in the bottoms stream, may be recycled to the catalytic cracking zone to enhance the overall conversion. Resid fluid catalytic cracking (RFCC) is a catalytic cracking process that is similar to FCC as discussed above, but modified to target heavy hydrocarbon feedstocks with a greater coking tendency by utilizing two catalyst regeneration stages and catalyst cooling to accommodate the enhanced regeneration requirements, including a high heat of coke combustion. Other related catalytic cracking processes are also known in the art and include RCC, MSCC$^{SM}$, PetroFCC$^{SM}$, and others, from which propylene-containing catalytic cracking products may be obtained and utilized in integrated processes according to the present invention. A common feature of such processes is the use of a hydrogen deficient atmosphere in the reaction zone, resulting in the generation of one or more catalytic cracking products containing propylene and normally other olefins.

A flow scheme according to aspects of the invention is shown in FIG. 1. In this illustrative embodiment, heavy hydrocarbon feedstock 2 such as VGO is passed to catalytic cracking process 300 to provide propylene-containing product 4, which generally also comprises $C_4$ olefins (e.g., normal 1- and 2-butenes and/or isobutylene). Propylene-containing product 4 is therefore a catalytic cracking product that may be obtained, for example, from contacting heavy hydrocarbon feedstock 2 with a catalyst of a fluid catalytic cracking (FCC) process as discussed above. Propylene-containing product 4 is processed together with fraction 6 (e.g., a liquid fraction) of an effluent from a dehydrogenation reaction zone of catalytic dehydrogenation process 100. Dehydrogenation reaction zone effluent fraction 6 is a propylene-containing product of catalytic dehydrogenation process 100, and hydrocarbon feed 8 to propylene recovery unit (PRU) 200 comprises both of these propylene containing products 4,6. As discussed above, dehydrogenation reaction zone effluent fraction 6 is normally obtained as a liquid fraction, containing propane and propylene, of the total effluent from the reaction zone of dehydrogenation process 100. The net hydrogen produced in catalytic dehydrogenation process 100 is contained in net off gas 20, which is a non-recycled portion of a vapor fraction of the dehydrogenation reaction zone effluent.

PRU 200, processes hydrocarbon feed 8 comprising catalytic cracking product 4 and a catalytic dehydrogenation product, namely dehydrogenation reaction zone effluent fraction 6 to provide PRU products comprising purified propylene fraction 10 and purified propane fraction 12. In the normal case where catalytic cracking product 4 is a liquefied petroleum gas (LPG) comprising $C_4$ olefins in addition to propylene, an additional PRU product is generally a $C_4$ olefin-enriched fraction 14 that may be sent for further processing (e.g., in the production of methyl tertiary butyl ether, MTBE). A further PRU product is a $C_2^-$ hydrocarbon enriched fraction 16 (i.e., enriched in methane, ethane, and ethylene). The designation of a fraction as being enriched in various components means that the fraction contains a higher concentration (e.g., measured in percent by volume) of those components, relative to the hydrocarbon feed 8 to the PRU 200. Likewise, fractions 10, 12, 14, and 16 also contain higher concentrations of propylene, propane, $C_4$ olefins, and $C_2^-$ hydrocarbons, respectively, than the feeds to the individual fractionation or distillation columns used to provide the fractions, as discussed in greater detail below.

PRU 200 generally includes a selective hydrogenation process for the conversion of diolefins (e.g., butadiene) and other highly unsaturated byproducts (e.g., acetylene) of catalytic dehydrogenation process 100 to more desirable (and less reactive), corresponding monoolefins. A representative selective hydrogenation process for converting diolefins to monoolefins is described, for example, in U.S. Pat. No. 4,695,560, with respect to a selective hydrogenation catalyst comprising nickel and sulfur dispersed on an alumina support material having a high surface area.

Selective hydrogenation is normally performed with a selective hydrogenation zone being maintained under relatively mild hydrogenation conditions, including an absolute pressure from about 280 kPa (40 psia) to about 5500 kPa (800 psia), with a range from about 350 kPa (50 psia) to about 2100 kPa (300 psia) being preferred. Relatively moderate selective hydrogenation zone temperatures, for example, from about 25° C. (77° F.) to about 350° C. (662° F.), preferably from about 50° C. (122° F.) to about 200° C. (392° F.), are representative. The liquid hourly space velocity (LHSV) is typically greater than about 1 $hr^{-1}$, and preferably greater than about 5 $hr^{-1}$ (e.g., between about 5 and about 35 $hr^{-1}$). The LHSV, closely related to the inverse of the reactor residence time, is the volumetric liquid flow rate over the catalyst bed divided by the bed volume and represents the equivalent number of catalyst bed volumes of liquid processed per hour. An important variable in selective hydrogenation is the ratio of makeup hydrogen to diolefins in the hydrocarbon feed to the selective hydrogenation process. To avoid the undesired saturation of a significant proportion of the monoolefins, generally less than about 2 times the stoichiometric hydrogen requirement for diolefin saturation is used.

Selective hydrogenation therefore requires the addition of makeup hydrogen 18 that can have varying levels of purity, depending on the source. An optional feed stream to the integrated processes described herein is propane-rich LPG stream 25 obtained, for example, from a natural gas plant that is often an industrial source of propane for catalytic dehydrogenation process 100 to produce propylene. Such a propane-rich LPG stream generally comprises at least about 50% by weight propane with only a minor amount (e.g., less than about 5% by weight) of propylene. As shown in FIG. 1, propane-rich LPG stream 25 may be combined with hydrocarbon feed 8 that is processed in PRU 200 or with other process streams or apparatuses of PRU, as discussed in more detail below. Alternatively, optional propane-rich LPG stream 25 can be a component of the feed to catalytic dehydrogenation process 100, together with purified propane fraction 12.

As is apparent in FIG. 1, purified propane fraction 12, catalytic dehydrogenation product 6, and hydrocarbon feed 8 to PRU 200 provide a recycle loop that advantageously allows, in a continuous manner, (i) recovery of propylene from the propylene-containing product 4 of catalytic cracking (e.g., LPG recovered from FCC and comprising predominantly propylene and $C_4$ olefins) and (ii) recycle of propane from this propylene-containing product 4 to extinction or near extinction by conversion to propylene in catalytic dehydrogenation process 100. In representative embodiments, for example, the overall conversion of propane in the LPG from FCC, comprising propane, propylene, and $C_4$ olefins, is at least about 90%, and often at least about 95%. Moreover, the integration of catalytic dehydrogenation process 100 with PRU 200 provides significantly improved economics over the case of a conventional, stand alone dehydrogenation process utilizing propane from FCC as a feed. In many cases, this source of propane would not provide sufficient capacity to render catalytic dehydrogenation economically feasible at all.

Figure 2:
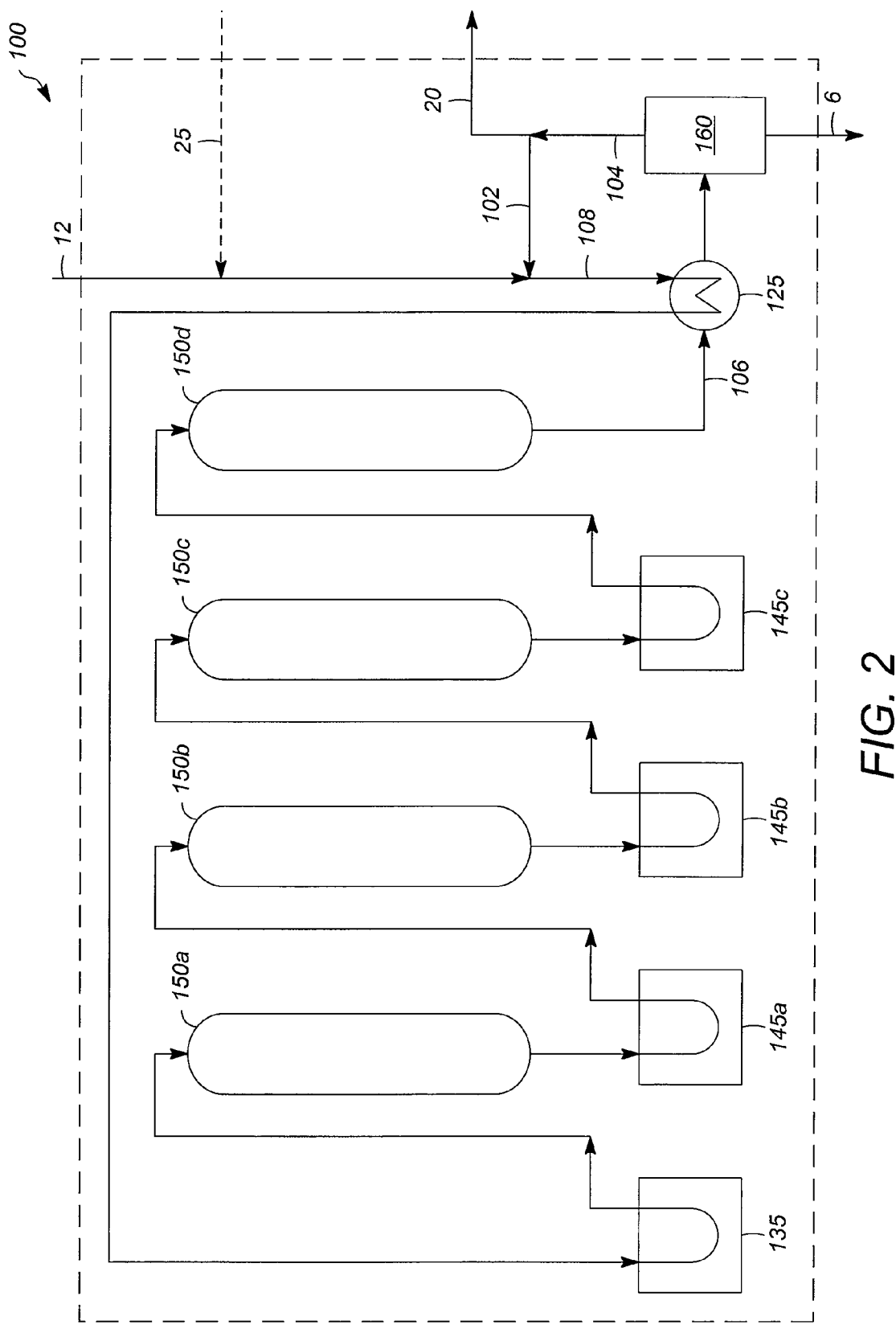
FIG. 2 depicts a representative catalytic dehydrogenation process in the integrated process shown in FIG. 1.

FIG. 2 depicts a representative catalytic dehydrogenation process 100 that may be used in the integrated process illustrated generally in FIG. 1. As noted above, purified propane fraction 12 and optionally propane-rich LPG stream 25 are passed as feeds to catalytic dehydrogenation process 100. Purified propane fraction 12 is normally combined with a recycled portion 102 of vapor fraction 104 of effluent 106 of the reaction zone of dehydrogenation process 100. A non-recycled portion of this vapor fraction 104 is net off gas 20, which contains the net hydrogen produced in catalytic dehydrogenation process 100. The combined dehydrogenation feed 108 is then passed to dehydrogenation combined feed/effluent heat exchanger 125 and further heated with preheater 135 prior to entering the dehydrogenation reaction zone comprising four dehydrogenation reactors 150a-150d in series, as depicted in the specific embodiment of FIG. 2.

In operation, dehydrogenation reactors 150a-150d often contain moving beds of catalyst. The dehydrogenation catalyst is passed serially through the reactors 150a-150d and spent or coked catalyst exiting the last reactor 150d is then regenerated by known methods for continuous catalyst regeneration (CCR) before being returned as regenerated catalyst to the first reactor 150a in the series. The catalyst circulation loop is not shown for simplicity. Interstage heaters 145a-145c between reactors 150a-150d compensate for the temperature drop across each reactor due to the main dehydrogenation reaction (i.e., the conversion of propane to propylene) being endothermic. Effluent 106 of the reaction zone of dehydrogenation process 100 is then cooled with the combined dehydrogenation feed 108 in combined feed/effluent heat exchanger 125. The effluent 106 from the dehydrogenation reaction zone is introduced to cryogenic separator 160 to obtain fraction 6 of dehydrogenation reaction zone effluent 106 comprising propane and propylene, which is normally obtained as a liquid fraction.

Dehydrogenation process 100 therefore includes a reaction zone (e.g., comprising multiple reactors and interstage heaters) and a separation zone (e.g., comprising a cryogenic separation separator 160) that provides, respectively, $C_3$ hydrocarbon-rich fraction 6 and hydrogen-rich vapor fraction 104, respectively, of the total dehydrogenation reaction zone effluent 106. According to embodiments of the invention, dehydrogenation process 100 does not include the capital cost- and energy-intensive fractionation towers used to purify product propylene and recover propane from fraction 6 for recycle back to the dehydrogenation reaction zone. These separation functions are advantageously performed using PRU 200 that is usually necessary in any event for recovery of propylene from propylene-containing product 4 of catalytic cracking process 300. Integration of PRU 200 with catalytic dehydrogenation process 100 therefore provides economic efficiencies as discussed above, even recognizing that the capacity of PRU 200 is increased, relative to the case of separate (i.e., non-integrated) cracking and dehydrogenation processes. According to particular embodiments of the invention, therefore, catalytic dehydrogenation process 100 consists essentially of a dehydrogenation reaction zone and a cryogenic separation zone, without fractionation towers.

Figure 3:
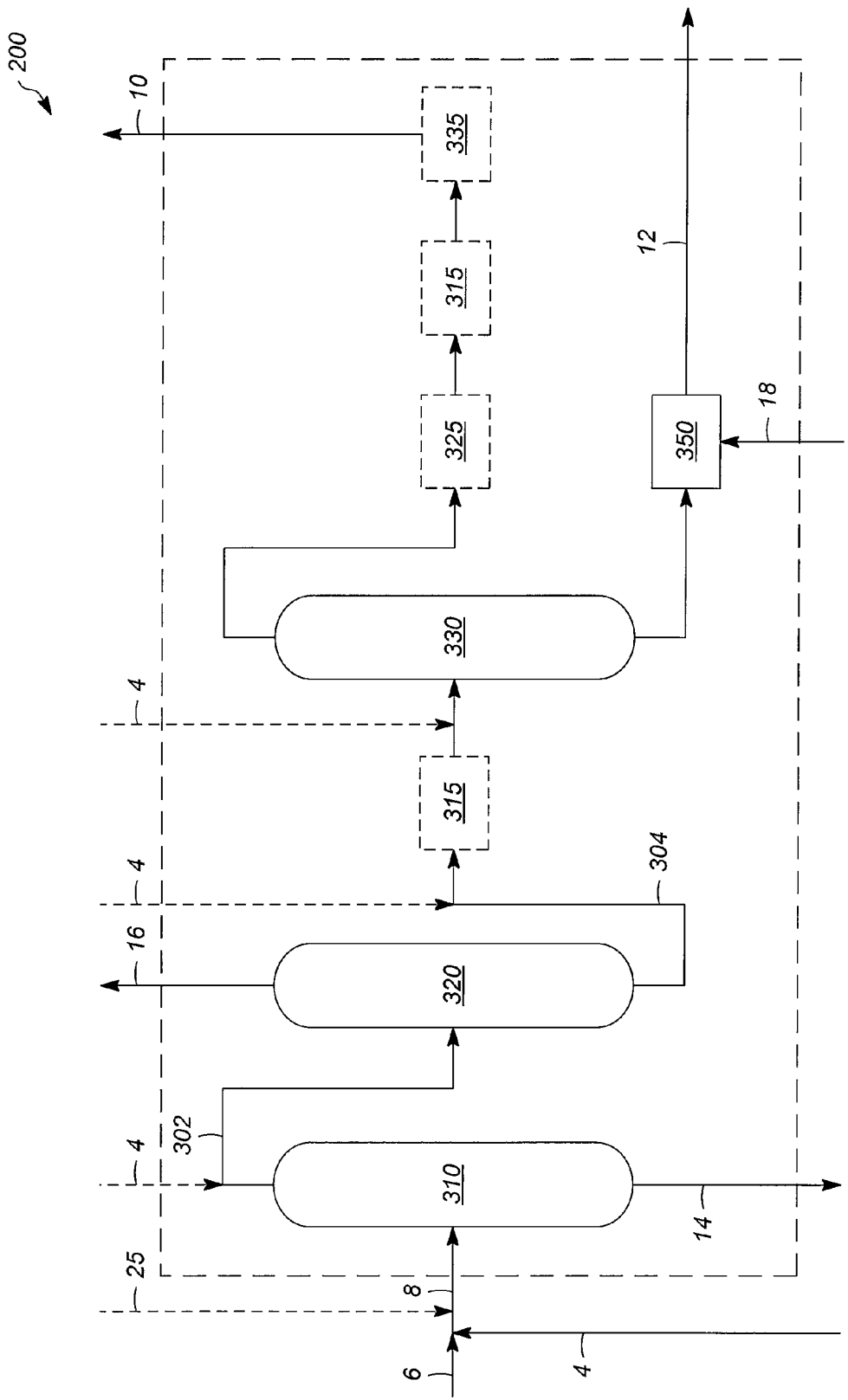
FIG. 3 depicts a representative PRU in the integrated process shown in FIG. 1.

A PRU 200 according to an embodiment of the invention is illustrated in FIG. 3. PRU comprises a fractionation section that includes depropanizer (e.g., $C_3/C_4$ splitter) 310, deethanizer 320, and propane/propylene splitter 330. As discussed above, propylene-containing products 4,6 of catalytic cracking and catalytic dehydrogenation are combined as a hydrocarbon feed 8, optionally with propane-rich LPG stream 25, and passed to depropanizer 310 to provide low-boiling depropanizer fraction 302 that is enriched in propylene, propane, and $C_2$– hydrocarbons, relative to hydrocarbon feed 8. Also, $C_4$ olefin-enriched fraction 14 (having a higher $C_4$ olefin concentration than hydrocarbon feed 8) is removed as a high-boiling fraction from depropanizer 310. Low-boiling depropanizer fraction 302 is then passed to deethanizer 320 to provide a low-boiling deethanizer fraction that is enriched in C$_2$- hydrocarbons relative to the feed to deethanizer, namely low-boiling depropanizer fraction 302. The low-boiling deethanizer fraction is therefore namely C$_2$- hydrocarbon enriched fraction 16 as a product of PRU 200. Also obtained from deethanizer 320 is high-boiling deethanizer fraction 304 enriched in propylene and propane relative to the feed to the deethanizer 320. High boiling deethanizer fraction 304 is then passed to a third fractionation column, namely propane/propylene splitter 330 that provides purified propylene fraction 10 and purified propane fraction 12 as low-boiling and high-boiling fractions, respectively, of propane/propylene splitter 330, which are also net products of PRU 200.

In addition to the fractionation section of PRU 200, FIG. 3 also illustrates an optional treating section comprising a conventional carbonyl sulfide (COS) removal system 325 that utilizes a suitable solvent to reduce the level of this contaminant if necessary. Other possible treating section systems include water removal or adsorbent drier system 315 and metals removal system 335 for reducing amounts of metals (e.g., antimony), which are often present as metal hydrides such as arsine and phosphine. As illustrated in FIG. 3, drier system 315 may be used to dry purified propylene fraction 10 alone and/or may optionally be positioned upstream of propane/propylene splitter 330 in order to additionally dry purified propane fraction 12 and thereby potentially obviate the need for driers on the feed to catalytic dehydrogenation process 100. According to particular embodiments of the invention, COS removal system 325, drier system 315, and metals removal system 335 together provide purified propylene fraction 10 that is a treated propylene product, preferably having a purity of at least about 99% by volume, and often at least about 99.5% by volume to meet polymer grade specifications.

In other embodiments, the propylene purity may be lower, depending on the end use of this product. For example, a purity of at least about 97% by volume (e.g., in the range from about 97% to about 99% by volume) or at least about 98% by volume (e.g., in the range from about 98% to about 99% by volume) may be acceptable for a non-polymer technology such as acrylonitrile production, or otherwise for polypropylene production processes that can accommodate a lower purity propylene. In yet further embodiments in which the propylene purity is below 97% (e.g., in the range from about 90% to about 95% by volume) it may be desirable to include selective hydrogenation (not shown) of the purified propylene fraction 10, in the manner discussed above with respect to converting highly unsaturated byproducts of dehydrogenation. In this case, selective hydrogenation of purified propylene fraction 10 would involve, for example, converting methyl acetylene and/or propadiene that may contaminate the propylene product removed from the propane/propylene splitter at propylene purities below about 97% by volume. Selective hydrogenation in such an embodiment may be used alone or together with any combination or all of the COS removal system 325, drier system 315, and metals removal system 335 described above.

FIG. 3 further illustrates the use of selective hydrogenation process 350 that utilizes makeup hydrogen 18, as discussed above, in order to selectively hydrogenate diolefins and acetylene and other undesirable byproducts contained in purified propane fraction 12 prior to its introduction into catalytic dehydrogenation process 100. It can also be seen in FIG. 3 that various optional addition points of propylene-containing product 4 of catalytic cracking process 300 to PRU 200 are possible. These possible addition points include low-boiling depropanizer fraction 302 and high-boiling deethanizer fraction 304, either upstream or downstream of optional drier system 315. Combinations of addition points are also possible, as well as addition directly to deethanizer 320 and/or propane/propylene splitter 330. Also, the various addition points of propylene-containing product 4 of catalytic cracking are applicable as addition points of propane-rich LPG stream 25, if used.

Figure 4:
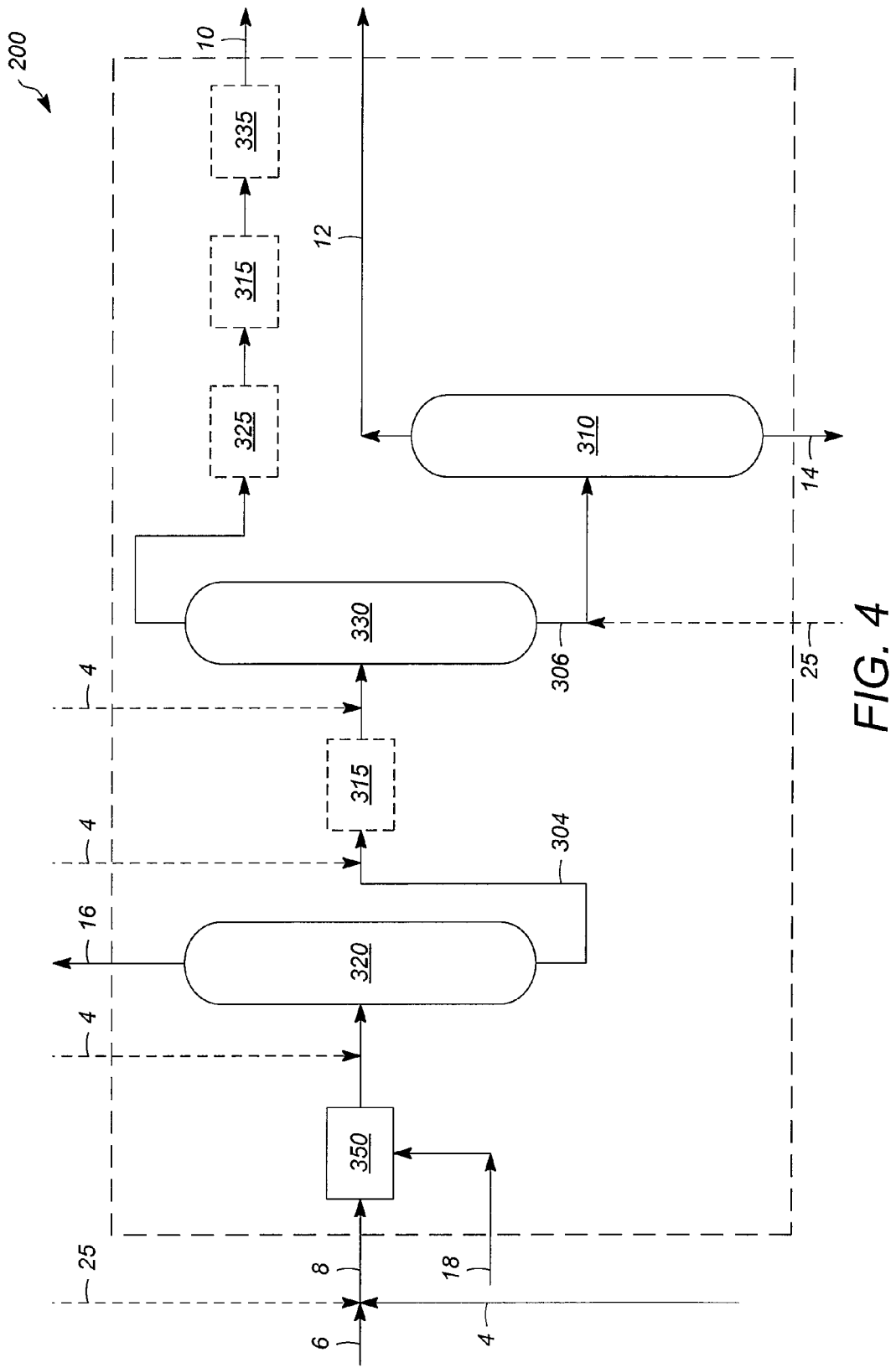
FIG. 4 depicts a representative alternative PRU in the integrated process shown in FIG. 1.

FIG. 4 illustrates an alternative configuration of PRU 200, in which hydrocarbon feed 8 as a combination of propylene-containing products 4,6 of catalytic cracking and catalytic dehydrogenation are passed to selective hydrogenation process 350 for byproduct removal prior to being fed to deethanizer 320 to provide C$_2$- hydrocarbon enriched fraction 16 and high-boiling deethanizer fraction 304 as discussed above. High-boiling deethanizer fraction 304 is optionally dried using drier system 315 prior to its introduction to propane/propylene splitter 330 that recovers purified propylene fraction 10 as discussed above, optionally as a treated propylene product following treatment in systems 325, 315, 335 for COS, water, and metals removal. Purified propane fraction 12 and C$_4$ olefin-enriched fraction 14 are recovered as a high- and low-boiling fractions, respectively, from depropanizer 310 that is used to fractionate high-boiling fraction 306 obtained from propane/propylene splitter 330.

As in FIG. 3, alternate addition points of propylene-containing product 4 of catalytic cracking process 300 are illustrated. This propylene-containing product 4 may be added, for example, directly to, or upstream of, deethanizer 320, or directly to, or upstream of, propane/propylene splitter 330, either before or after optional drying system 315. Again, these optional addition points also serve as optional addition points of propane-rich LPG stream 25, if used, as well as a further optional addition point of this stream being directly to, or upstream of depropanizer 310. In the embodiments shown in FIGS. 3 and 4, the low-boiling and high-boiling fractions of depropanizer 310, deethanizer 320, and propane/propylene splitter 330 are generally removed as overhead and bottoms products of these fractionation columns, but according to some embodiments they may also be removed as side cuts.

Aspects of the invention relate to integrated processes for the catalytic dehydrogenation of at least a portion of propane that is obtained (e.g., in an olefinic LPG product stream or other product) from a catalytic cracking process (e.g., FCC). Embodiments of the invention are therefore directed to integrated propylene production methods comprising processing, in a PRU, (i) a liquefied petroleum gas (LPG) comprising propylene and C$_4$ olefins, as a product of a fluid catalytic cracking (FCC) process, in combination with (ii) an effluent from a dehydrogenation reaction zone, comprising propylene and propane, as a product of a catalytic dehydrogenation process, to provide a purified propylene fraction and a purified propane fraction. The purified propane fraction is recycled to the catalytic dehydrogenation process. In particular embodiments of the integrated PRU/catalytic dehydrogenation processes described herein, the duplication of one or more fractionation towers used to perform relatively difficult hydrocarbon separations in conventional, separate propylene recovery and dehydrogenation processes is advantageously avoided. The integrated processes, as a combination of a PRU and catalytic dehydrogenation process, often have only a single depropanizer column, a single deethanizer column, and/or a single propane/propylene splitter column. In many cases only a single one of each of these columns is employed, thereby achieving significant cost advantages over conventional processes.

Those having skill in the art, with the knowledge gained from the present disclosure, will recognize that various changes can be made in the above integrated processes without departing from the scope of the present disclosure. The following example is representative of the present invention and its associated advantages and is not to be construed as limiting the scope of the invention as set forth in the appended claims.

EXAMPLE 1

In the case of a commercial catalytic dehydrogenation process, namely the UOP Oleflex™ process for production of propylene from propane, the product fractionation section comprising a depropanizer, a deethanizer, and a propane/propylene splitter, was estimated to represent about 25% of the total erected cost of a unit for 250 kMTA of propylene production. This fractionation section can be effectively eliminated by increasing the capacity of a PRU used to process LPG from FCC for propylene recovery. The overall capital cost savings of integrating a PRU with an Oleflex™ process to consolidate the fractionation sections of these processes, according to the present invention, is estimated to be about 10-15%. This savings can be sufficient to render smaller capacity processes for propylene production economically feasible, depending on the price of propylene relative to propane and other factors.

The invention claimed is:

1. An integrated method for propylene production and recovery, comprising:
   (a) processing, in a propylene recovery unit (PRU), a hydrocarbon feed comprising propylene-containing products of both a catalytic cracking process and a catalytic dehydrogenation process, to provide PRU products comprising a purified propylene fraction and a purified propane fraction wherein the PRU comprises multiple fractionation units, and includes a dewatering unit after a deethanizer and a dewatering unit after a propane/propylene splitter;
   (b) selectively hydrogenating diolefins and acetylenes in the purified propane fraction, thereby generating a purified propane fraction with reduced diolefins and acetylenes;
   (c) passing the purified propane fraction with reduced diolefins and acetylenes to the catalytic dehydrogenation process, thereby generating a liquid product stream comprised substantially of propylene and propane; and
   (d) passing the liquid product stream back to the PRU; wherein the overall conversion of propane in the product from the catalytic cracking process is at least about 90%.

2. The method of claim 1, wherein the catalytic cracking process is a fluid catalytic cracking (FCC) process.

3. The method of claim 1, wherein the liquid fraction is obtained from a cryogenic separation of the effluent from the dehydrogenation reaction zone.

4. The method of claim 3, wherein step (b) comprises passing the purified propane fraction to the dehydrogenation reaction zone in combination with a recycled portion of a vapor fraction, comprising predominantly hydrogen, obtained from the cryogenic separation.

5. The method of claim 1, wherein the propylene-containing product of the catalytic cracking process is a liquefied petroleum gas (LPG) comprising propylene and $C_4$ olefins.

6. The method of claim 5, wherein the PRU products further comprise a fraction enriched in the $C_4$ olefins.

7. The method of claim 6, wherein the PRU comprises a fractionation section comprising a depropanizer, a deethanizer, and a propane/propylene splitter.

8. The method of claim 7, wherein step (a) comprises:
   (i) passing the hydrocarbon feed to the depropanizer to provide a low-boiling depropanizer fraction enriched in propylene, propane, and $C_2-$ hydrocarbons and the fraction enriched in the $C_4$ olefins;
   (ii) passing the low-boiling depropanizer fraction to the deethanizer to provide a low-boiling deethanizer fraction enriched in the $C_2-$ hydrocarbons and a high-boiling deethanizer fraction enriched in propylene and propane; and
   (iii) passing the high-boiling deethanizer fraction to the propane/propylene splitter to provide the purified propylene fraction and the purified propane fraction.

9. The method of claim 7, wherein the PRU further comprises a treating section comprising systems for the removal of impurities selected from the group consisting of carbonyl sulfide, water, metals, and combinations thereof.

10. The method of claim 1, wherein the hydrocarbon feed further comprises a propane-rich LPG stream.

11. An integrated method for producing propylene, the method comprising:
    (a) contacting a heavy hydrocarbon feedstock with a fluidized cracking catalyst to provide a catalytic cracking product comprising propylene and $C_4$ olefins;
    (b) processing, in a propylene recovery unit (PRU), the catalytic cracking product and a catalytic dehydrogenation product, to provide PRU products comprising a purified propylene fraction and a purified propane fraction wherein the PRU comprises multiple fractionation units, and includes a dewatering unit after a deethanizer and a dewatering unit after a propane/propylene splitter;
    (c) selectively hydrogenating diolefins and acetylenes in the purified propane fraction thereby creating a purified propane fraction with reduced diolefins and acetylenes;
    (d) dehydrogenating the purified propane fraction having reduced diolefins and acetylenes in a catalytic dehydrogenation process to provide a catalytic dehydrogenation product, comprising substantially of propane and propylene; and
    (e) passing the dehydrogenation product back to the PRU to further separate and recycle the propane to substantially complete conversion to propylene; wherein the overall conversion of propane in the catalytic cracking product is at least about 90%.

12. The method of claim 11, wherein the heavy hydrocarbon feedstock comprises vacuum gas oil (VGO).

13. The method of claim 11, wherein step (b) comprises:
    (i) passing the catalytic cracking product and the catalytic dehydrogenation product to a depropanizer to provide a low-boiling depropanizer fraction enriched in propylene, propane, and $C_2-$ hydrocarbons and a high-boiling depropanizer fraction enriched in the $C_4$ olefins;
    (ii) passing the low-boiling depropanizer fraction to a deethanizer to provide a low-boiling deethanizer fraction enriched in the $C_2-$ hydrocarbons and a high-boiling deethanizer fraction enriched in propylene and propane; and
    (iii) passing the high-boiling deethanizer fraction to a propane/propylene splitter to provide the purified propylene fraction and the purified propane fraction.

14. The method of claim 13, further comprising treating the purified propylene fraction to remove carbonyl sulfide, water, and metals and provide a treated propylene product.

15. The method of claim 14, wherein the treated propylene product comprises propylene having a purity of at least about 97% by volume.

16. An integrated propylene production method comprising:
    (a) processing, in a propylene recovery unit (PRU), (i) a liquefied petroleum gas (LPG) comprising propylene and $C_4$ olefins, as a product of a fluid catalytic cracking (FCC) process, in combination with (ii) an effluent from a dehydrogenation reaction zone, comprising propylene and propane, as a product of a catalytic dehydrogenation process, to provide a purified propylene fraction and a purified propane fraction wherein the PRU comprises multiple fractionation units, and includes a dewatering unit after a deethanizer and a dewatering unit after a propane/propylene splitter;

(b) selectively hydrogenating diolefins and acetylenes in the purified propane fraction, thereby creating a purified propane stream with reduced diolefins and acetylenes;

(c) recycling the purified propane stream with reduced diolefins and acetylenes to the catalytic dehydrogenation process, thereby generating a dehydrogenation process stream comprising propylene and propane; and (d) passing the dehydrogenation process stream back to the PRU; wherein the overall conversion of propane in the LPG is at least about 90%.

17. The method of claim 16, wherein the catalytic dehydrogenation process and the PRU together have a single depropanizer fractionation column, a single deethanizer fractionation column, and a single propane/propylene splitter fractionation column.

18. The method of claim 16, wherein the overall conversion of propane, in the liquefied petroleum gas (LPG) comprising propylene and $C_4$ olefins, to propylene is at least about 90%.

* * * * *